(12) United States Patent
Hirsch

(10) Patent No.: US 9,532,858 B2
(45) Date of Patent: *Jan. 3, 2017

(54) INTRAORAL DEVICE AND METHOD OF USE

(71) Applicant: Innerlite, Inc., Santa Barbara, CA (US)

(72) Inventor: James A. Hirsch, Santa Barbara, CA (US)

(73) Assignee: Innerlite, Inc., Santa Barbara, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/169,367

(22) Filed: May 31, 2016

(65) Prior Publication Data

US 2016/0270890 A1 Sep. 22, 2016

Related U.S. Application Data

(63) Continuation of application No. 14/285,248, filed on May 22, 2014, now Pat. No. 9,358,086.

(51) Int. Cl.
*A61C 17/06* (2006.01)
*A61C 5/14* (2006.01)
*A61B 13/00* (2006.01)

(52) U.S. Cl.
CPC .............. *A61C 17/043* (2013.01); *A61B 13/00* (2013.01); *A61C 5/14* (2013.01)

(58) Field of Classification Search
CPC ....... A61C 17/043; A61C 17/04; A61C 5/007; A61C 5/14; A61C 17/00; A61C 17/14; A61C 19/00
USPC ....................... 433/91, 93, 29, 136, 138, 140
See application file for complete search history.

(56) References Cited

U.S. PATENT DOCUMENTS

| | | | |
|---|---|---|---|
| 1,122,086 A | 12/1914 | William | |
| 2,510,125 A | 6/1950 | Meakin | |
| 2,937,445 A * | 5/1960 | Erickson | A61B 1/24 433/93 |
| 3,090,122 A | 5/1963 | Erickson | |
| D210,583 S | 3/1968 | Westlund | |

(Continued)

FOREIGN PATENT DOCUMENTS

| | | |
|---|---|---|
| GB | 1017515 A | 1/1966 |
| WO | 2008064904 A1 | 6/2008 |

OTHER PUBLICATIONS

International Search Report and Written Opinion of PCT/US2015/032219, Korean Intellectual Property Office, Sep. 8, 2015, 16 pages.

(Continued)

*Primary Examiner* — Nicholas Lucchesi
(74) *Attorney, Agent, or Firm* — Procopio Cory Hargreaves and Savitch LLP

(57) ABSTRACT

An intraoral device includes a flexible body having an upper front flap including evacuation holes and a upper edge; an upper rear flap forming an upper pocket with the upper front flap and including internal channels and a upper edge separated from the upper edge of the upper front flap to form an upper pocket opening, the internal channels terminating in grooves along the upper edge; a lower front flap including evacuation holes and a lower edge; a lower rear flap forming a lower pocket with the lower front flap and including internal channels and a lower edge separated from the lower edge of the lower front flap to form an lower pocket opening, the internal channels terminating in grooves along the lower edge.

11 Claims, 10 Drawing Sheets

(56) References Cited

U.S. PATENT DOCUMENTS

| | | | |
|---|---|---|---|
| 3,396,468 A | 8/1968 | Dayhoff | |
| 3,864,831 A * | 2/1975 | Drake | A61C 17/043 433/91 |
| 3,881,254 A | 5/1975 | Epstein et al. | |
| 4,017,975 A | 4/1977 | Johnson | |
| 4,024,642 A | 5/1977 | Zorovich | |
| 4,167,814 A | 9/1979 | Schubert | |
| 4,240,789 A * | 12/1980 | Rosenthaler | A61C 17/043 433/136 |
| 4,259,067 A | 3/1981 | Nelson | |
| 4,425,911 A | 1/1984 | Luomanen et al. | |
| 4,495,945 A | 1/1985 | Liegner | |
| 4,583,527 A | 4/1986 | Musicant et al. | |
| 4,592,344 A | 6/1986 | Scheer | |
| 4,643,172 A | 2/1987 | Taff et al. | |
| 4,802,851 A | 2/1989 | Rhoades | |
| 4,865,545 A | 9/1989 | La Rocca | |
| D303,834 S | 10/1989 | Collins | |
| 4,906,188 A | 3/1990 | Moseley | |
| 4,975,057 A | 12/1990 | Dyfvermark | |
| 4,992,046 A | 2/1991 | Sharp | |
| 4,996,976 A | 3/1991 | Nakagawa | |
| 5,009,595 A | 4/1991 | Osborn | |
| 5,071,347 A | 12/1991 | McGuire | |
| 5,078,602 A | 1/1992 | Honoshofsky | |
| 5,127,411 A | 7/1992 | Schoolman et al. | |
| 5,152,686 A | 10/1992 | Duggan | |
| 5,232,362 A | 8/1993 | Kanas | |
| 5,281,134 A | 1/1994 | Schultz | |
| 5,366,489 A | 11/1994 | Burgio et al. | |
| 5,438,976 A | 8/1995 | Nash | |
| 5,462,435 A | 10/1995 | Young | |
| 5,496,363 A | 3/1996 | Burgio et al. | |
| 5,513,986 A | 5/1996 | Feltham et al. | |
| 5,516,286 A | 5/1996 | Kushner | |
| 5,588,836 A | 12/1996 | Landis et al. | |
| 5,725,370 A | 3/1998 | Himeno et al. | |
| 5,762,496 A | 6/1998 | Albertsson et al. | |
| 5,769,635 A | 6/1998 | Eldreth | |
| 5,827,061 A * | 10/1998 | Goodman | A61C 17/043 433/93 |
| 5,873,718 A | 2/1999 | Sullivan | |
| 5,890,899 A | 4/1999 | Sclafani | |
| 5,924,866 A | 7/1999 | Eldreth et al. | |
| 6,022,214 A * | 2/2000 | Hirsch | A61B 1/24 433/140 |
| 6,149,430 A | 11/2000 | Nemetz et al. | |
| 6,193,513 B1 | 2/2001 | Pancallo | |
| 6,213,772 B1 * | 4/2001 | Costello | A61C 17/043 433/140 |
| 6,244,866 B1 | 6/2001 | Campbell | |
| 6,267,591 B1 | 7/2001 | Barstow | |
| 6,338,627 B2 * | 1/2002 | Hirsch | A61C 5/14 433/140 |
| 6,379,147 B1 | 4/2002 | Georgakis et al. | |
| 6,575,746 B2 | 6/2003 | Hirsch et al. | |
| 6,634,884 B2 | 10/2003 | Phillips | |
| 6,652,276 B2 | 11/2003 | Fischer et al. | |
| 6,655,960 B2 | 12/2003 | Fischer | |
| 6,716,029 B2 | 4/2004 | Fischer et al. | |
| D491,663 S | 6/2004 | Bat-Genstein | |
| 6,743,017 B2 | 6/2004 | O'Neill | |
| D495,799 S | 9/2004 | Hirsch | |
| 6,908,308 B2 | 6/2005 | Hirsch et al. | |
| 6,939,134 B2 | 9/2005 | Sherry et al. | |
| 6,974,321 B2 * | 12/2005 | Hirsch | A61C 5/14 433/140 |
| 6,981,870 B2 | 1/2006 | Heasley | |
| 7,077,652 B2 | 7/2006 | Kilcher et al. | |
| D556,327 S | 11/2007 | Albelda | |
| 7,293,990 B2 | 11/2007 | Hirsch et al. | |
| 7,335,023 B2 * | 2/2008 | Mahlmann | A61C 17/043 433/136 |
| 7,611,354 B2 * | 11/2009 | Hirsch | A61C 1/088 433/93 |
| 7,748,981 B2 | 7/2010 | Hirsch et al. | |
| 8,029,280 B2 * | 10/2011 | Black | A61C 17/043 433/140 |
| 8,057,227 B2 | 11/2011 | Hirsch et al. | |
| 8,057,228 B2 | 11/2011 | Hirsch et al. | |
| 8,075,310 B2 | 12/2011 | Hirsch et al. | |
| 8,297,973 B2 | 10/2012 | Hirsch et al. | |
| 8,852,169 B2 * | 10/2014 | Milo | A61C 17/043 433/91 |
| 8,911,232 B2 * | 12/2014 | Nguyen | A61C 17/0208 433/136 |
| 2004/0033468 A1 | 2/2004 | Fischer | |
| 2006/0063129 A1 | 3/2006 | Hirsch | |
| 2007/0231773 A1 | 10/2007 | Pontynen et al. | |
| 2007/0259307 A1 | 11/2007 | Quan et al. | |
| 2008/0318183 A1 | 12/2008 | Suzman | |
| 2009/0246728 A1 * | 10/2009 | Hirsch | A61C 5/14 433/36 |
| 2011/0311942 A1 | 12/2011 | Black et al. | |
| 2014/0212837 A1 | 7/2014 | Nguyen et al. | |
| 2014/0212838 A1 | 7/2014 | Nguyen et al. | |
| 2014/0212839 A1 | 7/2014 | Nguyen et al. | |
| 2014/0212840 A1 | 7/2014 | Nguyen et al. | |
| 2014/0212841 A1 | 7/2014 | Nguyen et al. | |

OTHER PUBLICATIONS

International Search Report and Written Opinion of PCT/US2009/000903, European Patent Office, Jul. 22, 2009, 8 pages.

Frias Rdh, Mark, "*Izolation* vs. *IsoDry*", Jul. 3, 2011, accessed on Jan. 7, 2016 at http://markrdh.com/?p=147, 6 pages.

* cited by examiner

INTRAORAL DEVICE AND METHOD OF USE

CROSS-REFERENCE TO RELATED APPLICATION

This application is a continuation of pending application Ser. No. 14/285,248 filed May 22, 2014.

FIELD OF THE INVENTION

The invention relates, in general, to dental appliances, and, in particular, to dental appliances for vacuum suction of the mouth of a dental patient for examination and/or operative purposes.

BACKGROUND OF THE INVENTION

During dental examination and/or operation, a number of fluids, e.g., saliva from the parotid gland, blood, water from the dental equipment, are produced in the patient's mouth. It is important to remove these fluids for the comfort of the patient, to prevent fluids and material from being aspirated into the throat or lungs of the patient, and to assist the health care provider in observing and/or operating within the patient's mouth.

SUMMARY OF THE INVENTION

An aspect of the invention involves an intraoral device that removes fluids from all areas of the mouth, e.g., operating side, vestibule area on the operation side, the lingual vestibule (along the side of the tongue), contralateral side vestibule, eliminating the need for constant patient mouth rinsing and the need for a dental assistant to aspirate debris.

Another aspect of the invention involves an intraoral device comprising a flexible body comprising an upper front flap including evacuation holes and a upper edge; an upper rear flap forming an upper pocket with the upper front flap and including internal channels and a upper edge separated from the upper edge of the upper front flap to form an upper pocket opening, the internal channels terminating in grooves along the upper edge; a lower front flap including evacuation holes and a lower edge; a lower rear flap forming a lower pocket with the lower front flap and including internal channels and a lower edge separated from the lower edge of the lower front flap to form an lower pocket opening, the internal channels terminating in grooves along the lower edge, wherein in a non-vacuum state the upper pocket opening and lower pocket opening are open and in a vacuum state the upper pocket opening and lower pocket opening are substantially sealed closed so that aspiration of fluids from the patient's mouth occurs through the evacuation holes in the front flaps and grooves, which become fluid inlets for drawing fluids through the channels, of the rear flaps.

One or more implementations of the above aspect of the invention include one or more of the following: the evacuation holes are in the front flaps and not in the rear flaps; the grooves are in the rear flaps at an intersection of the edges and the internal channels of the rear flaps and not in the front flaps; the internal channels are vertical channels; the internal channels form corresponding external ridges in the rear flaps; the evacuation holes communicate with and are aligned with the internal channels; the intraoral device includes a horizontally and longitudinally extending spine, an upper internal evacuation channel disposed above the spine in the upper pocket, and a lower internal evacuation channel disposed below the spine in the lower pocket; and/or the intraoral device includes an upper portion above the spine and a lower portion below the spine that are vertically symmetrical.

Another aspect of the invention involves a method of using the intraoral device of the aspect of the invention (or one or more implementations) described above. The method comprises inserting the intraoral device into the patient's mouth so that the upper edges of the upper flaps contact an upper part of the patient's mouth and the lower edges of the lower flaps contact a lower part of tongue within the mouth of the patient; applying vacuum state to the intraoral device so that the upper pocket opening and lower pocket opening are substantially sealed closed and the grooves become fluid inlets for drawing fluids through the channels; and aspirating fluids from the patient's mouth through the evacuation holes in the front flaps and into the channels through the grooves.

Other, more particular features and advantages of the inventions are set forth in the following detailed description and drawings.

BRIEF DESCRIPTION OF THE DRAWINGS

The drawings illustrate both the design and utility of preferred embodiments of the present invention, in which similar elements are referred to by common reference numbers, wherein.

DETAILED DESCRIPTION OF PREFERRED EMBODIMENTS

Figure 1:
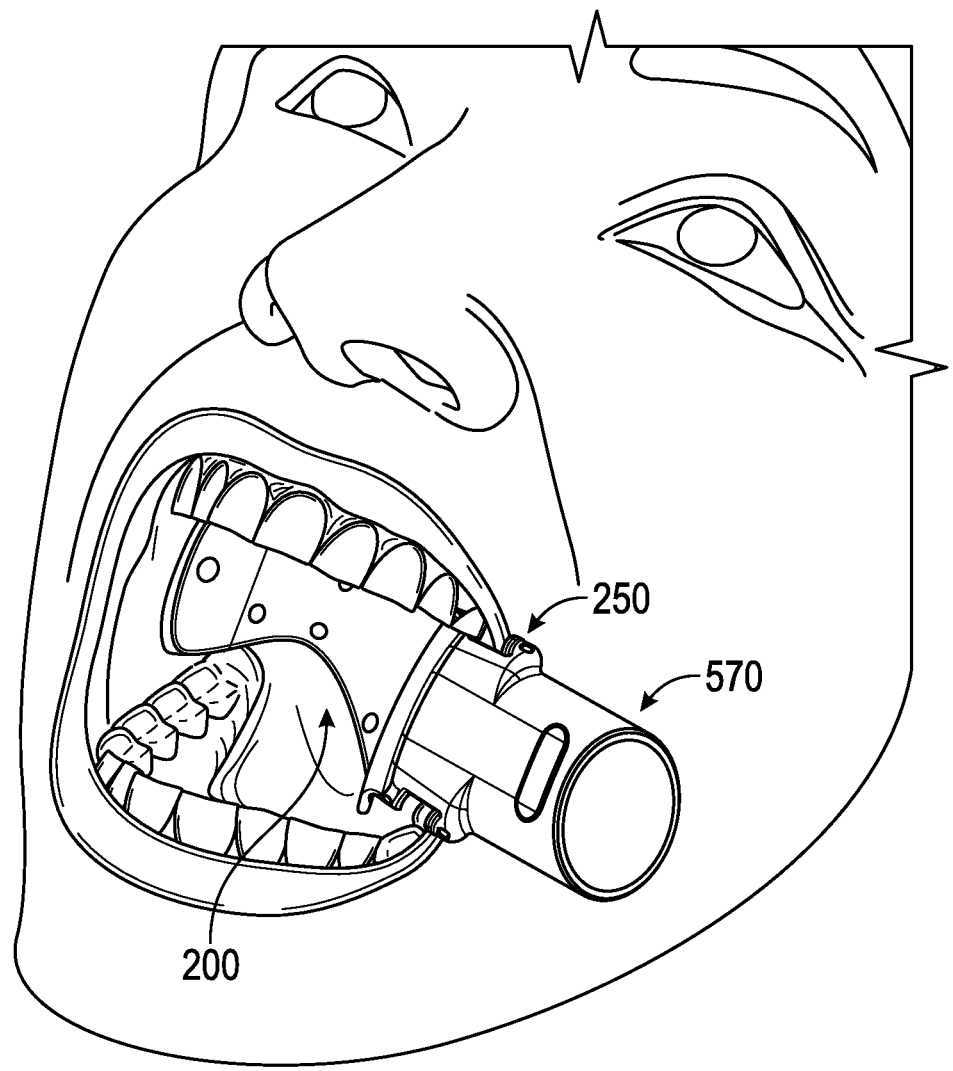
FIG. 1 is a front perspective view of an embodiment of the intraoral device shown inside a patient's mouth.
Figure 2:
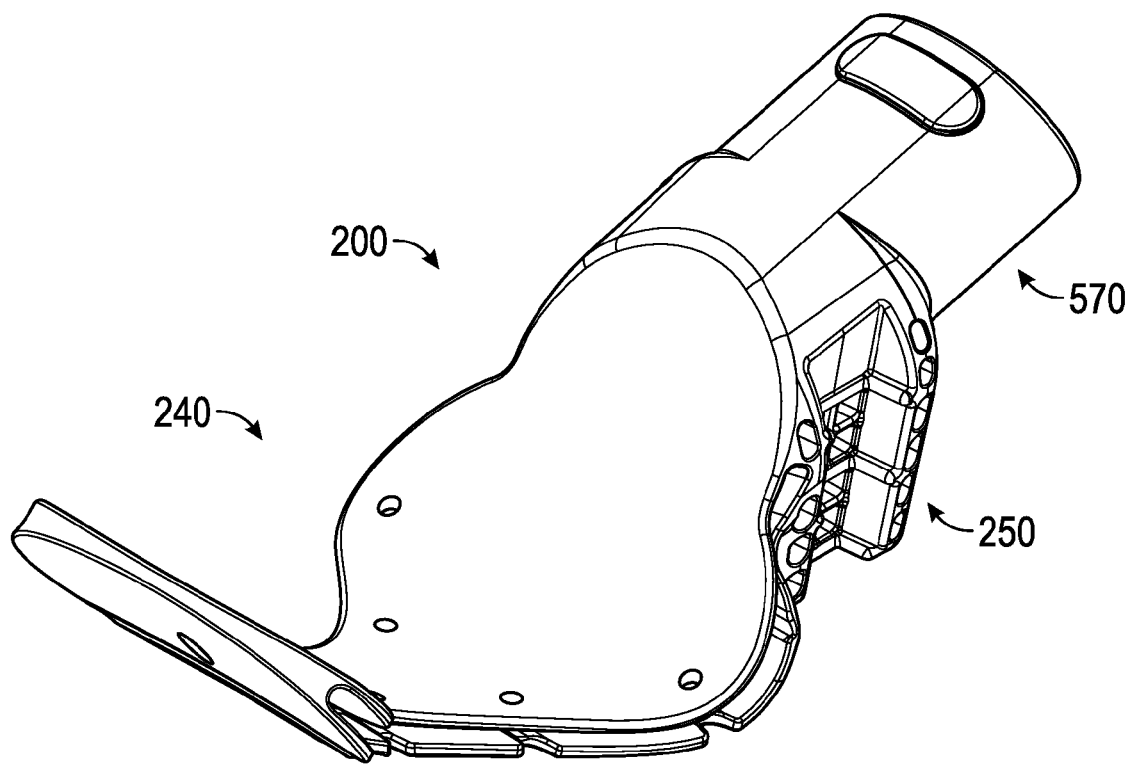
FIG. 2 is a front perspective view of the intraoral device.
Figure 3:
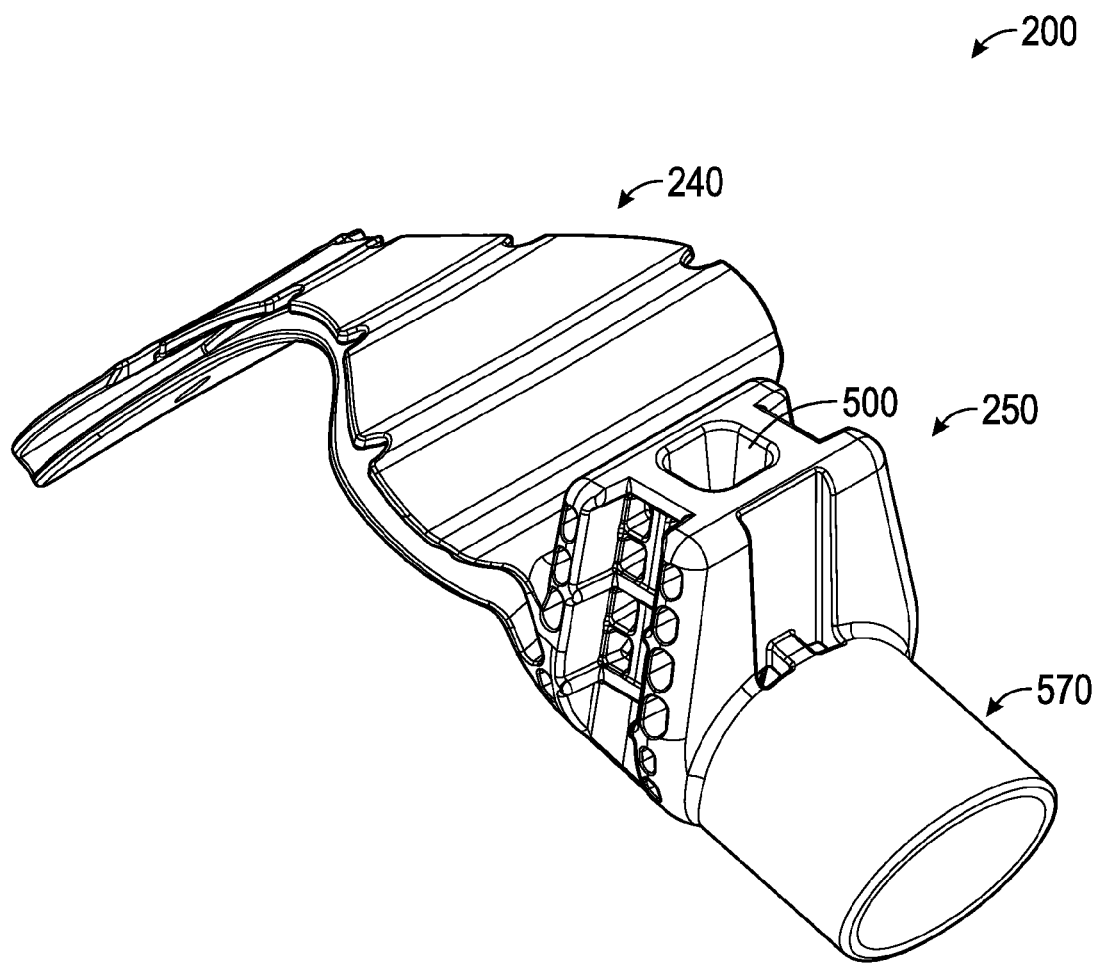
FIG. 3 is a rear perspective view of the intraoral device.
Figure 4:
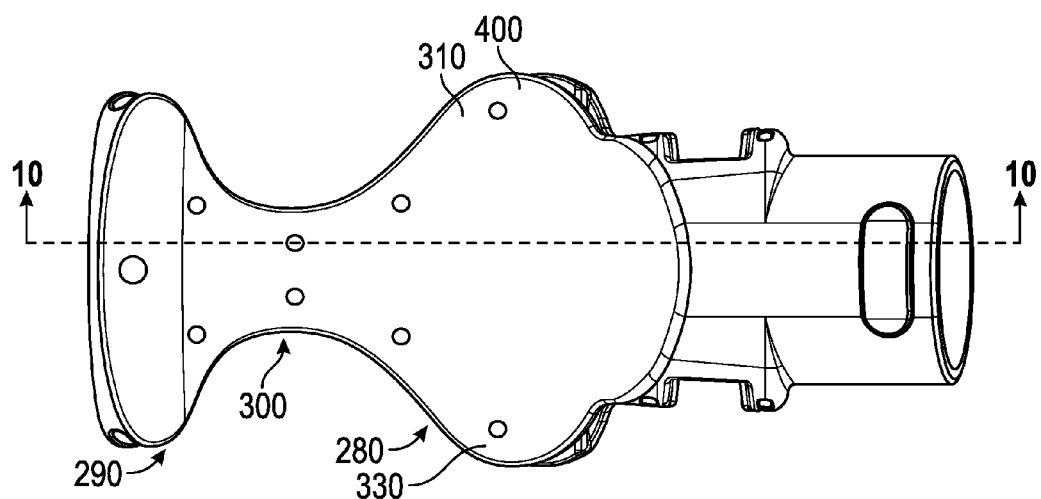
FIG. 4 is a front elevational view of the intraoral device.
Figure 5:
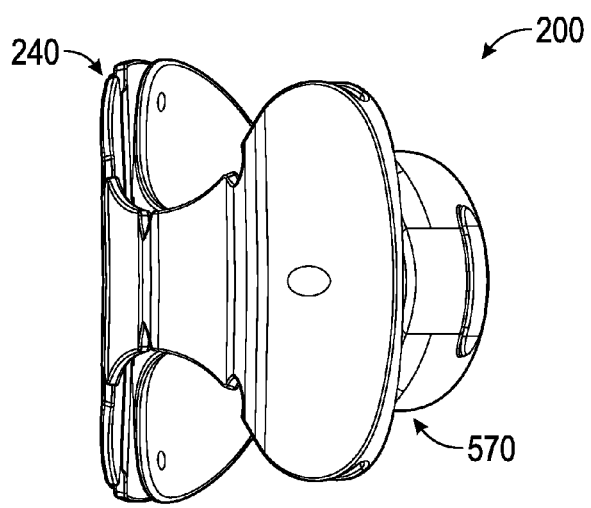
FIG. 5 is a left side elevational view of the intraoral device.
Figure 6:
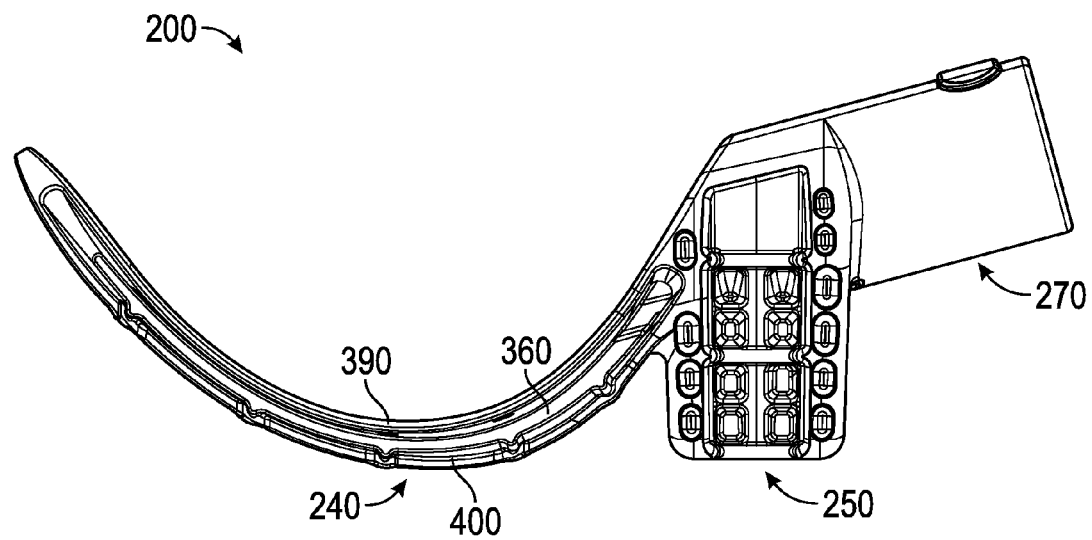
FIG. 6 is a bottom plan view of the intraoral device.
Figure 7:
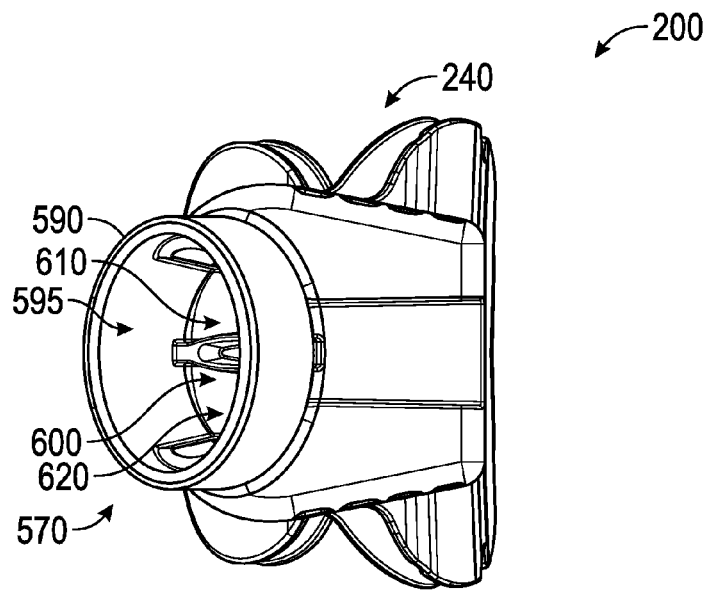
FIG. 7 is a right side elevational of the intraoral device.
Figure 8:
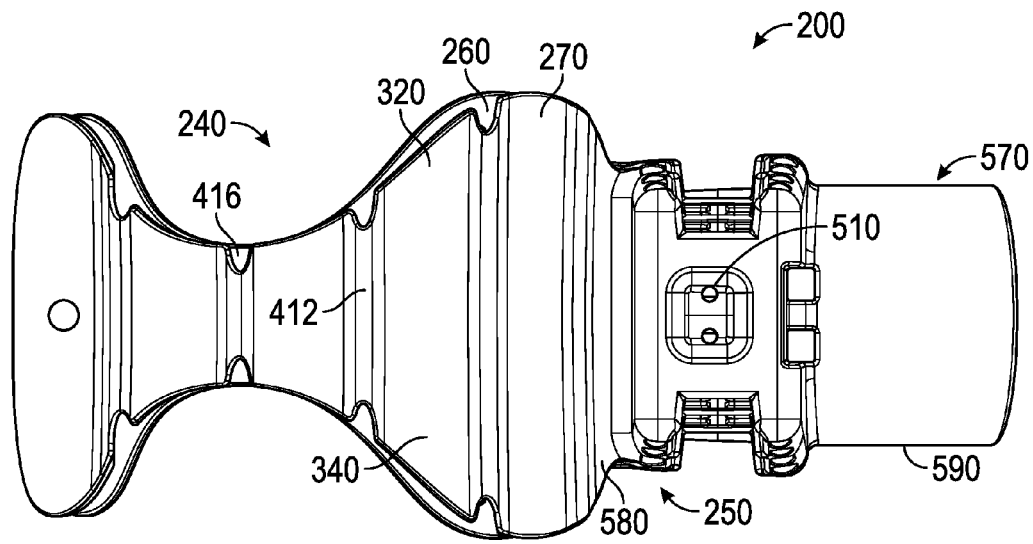
FIG. 8 Is a rear elevational view of the intraoral illumination device.
Figure 9:
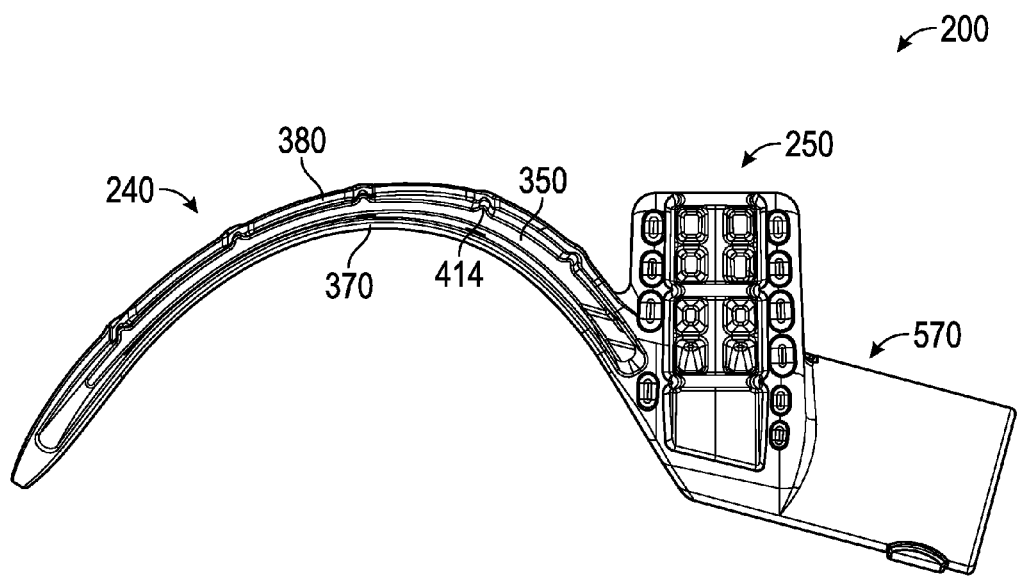
FIG. 9 is a top plan view of the intraoral device.
Figure 10:
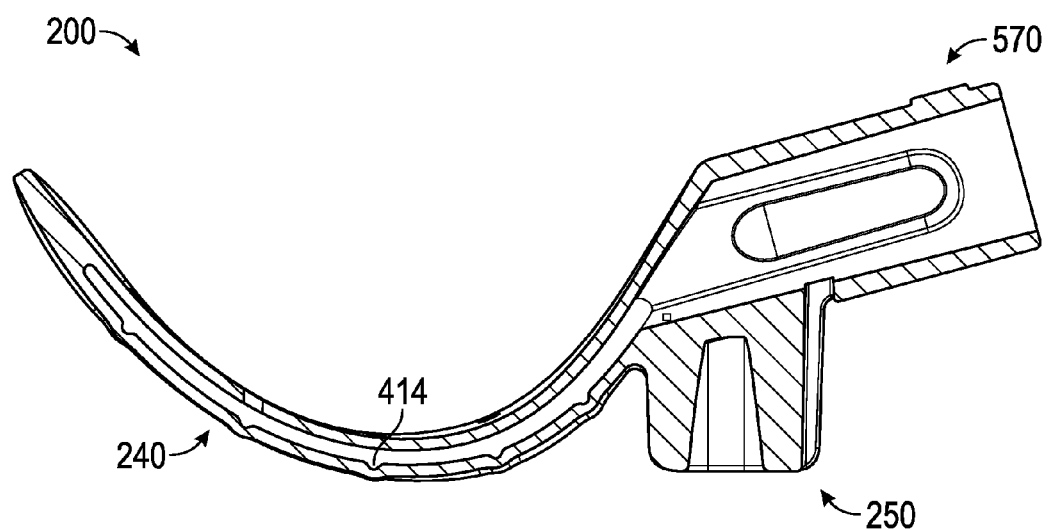
FIG. 10 is a cross-sectional view of the intraoral device taken along lines 10-10 of FIG. 4.
Figure 11:
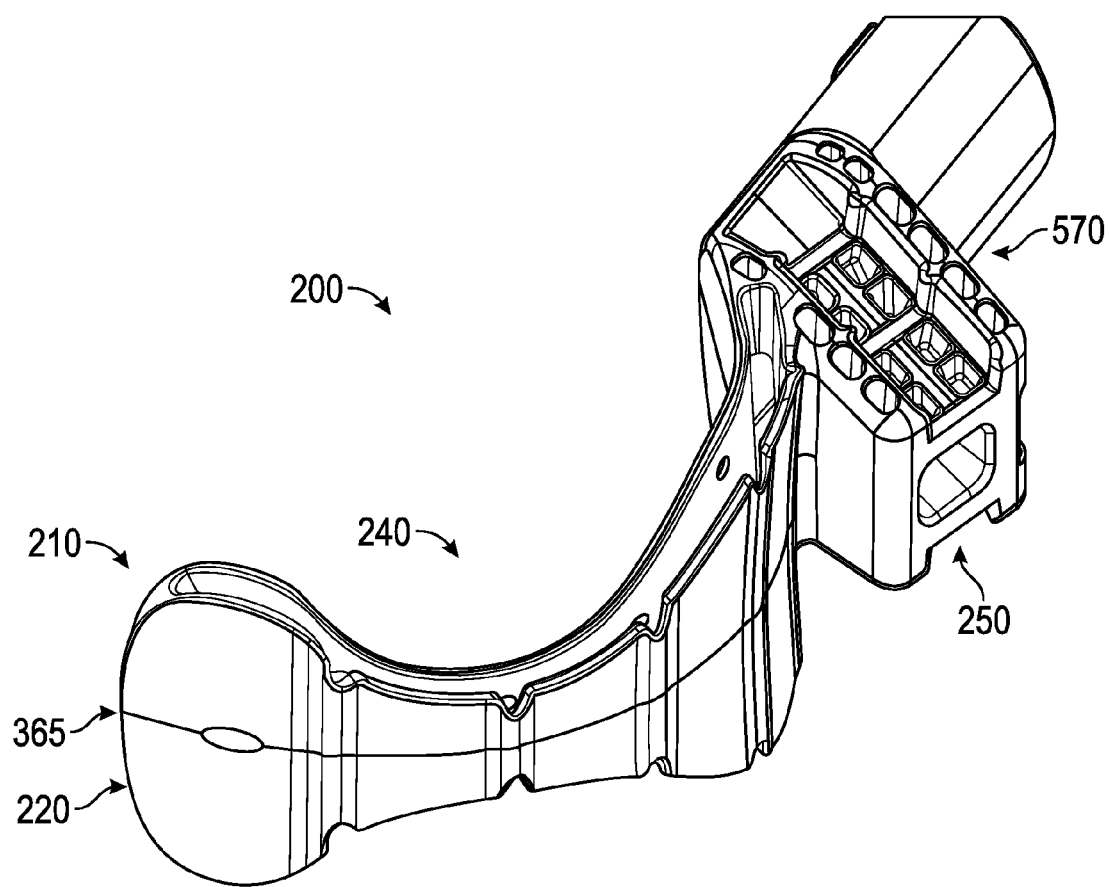
FIG. 11 is another rear perspective view of the intraoral device.
Figure 12:
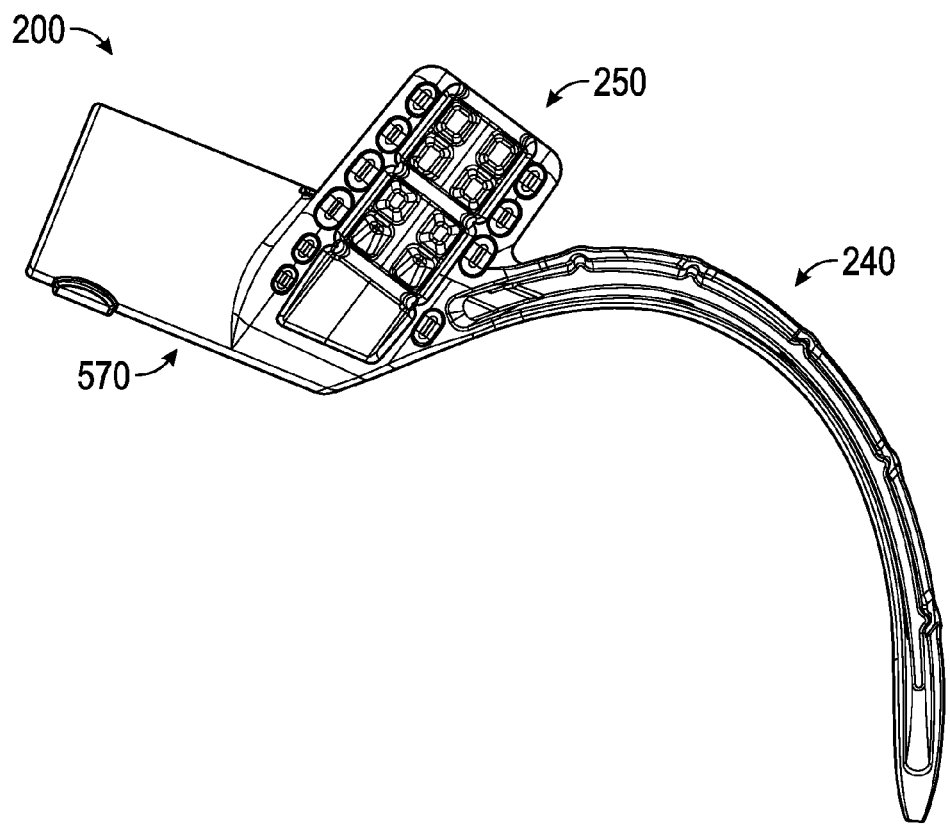
FIG. 12 is another plan view of the intraoral device.
Figure 13:
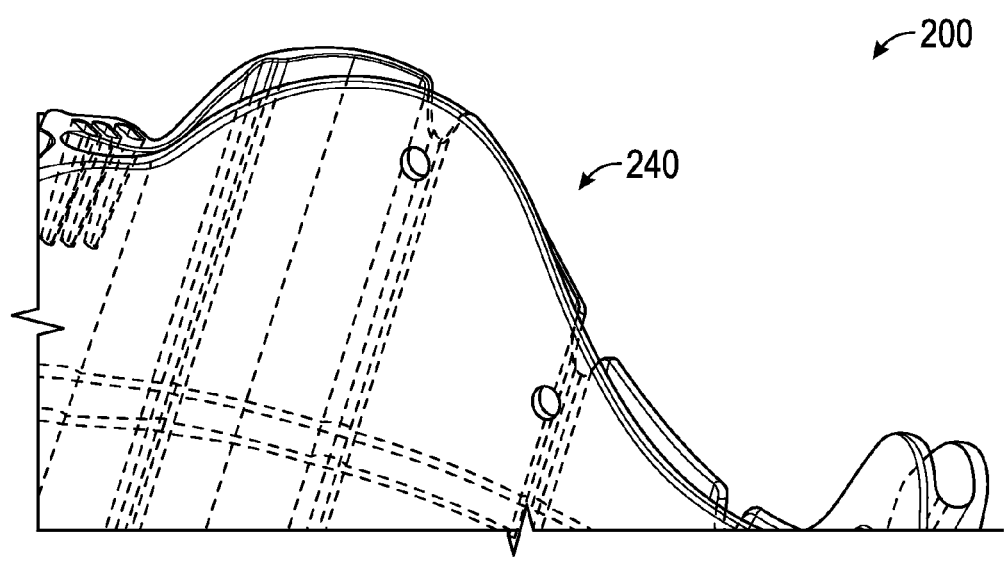
FIG. 13 is a partial perspective view of the intraoral device.

With reference to FIGS. 1-14, an embodiment of an intraoral device 200 that removes fluids from all areas of a patient's mouth 202 will now be described. The intraoral device 200 is preferably a one-piece, flexible, integrated molded body made of a single homogeneous material or combination of materials. The intraoral device 200 is preferably molded out of a translucent (e.g., transparent), flexible, soft, elastic, resilient, biocompatible thermoplastic elastomer. The intraoral device 200 is also vertically symmetrical so that an upper portion 210 is symmetric with respect to a lower portion 220 relative to spine 365. This allows the same intraoral device 200 to be positioned on either the left side or the right side of the patient's mouth. The intraoral device 200 may also come in different sizes for different-size mouths. The intraoral device 200 is also disposable after each use. The intraoral device 200 may be used to provide vacuum suction or the intraoral device 200 may be used to provide vacuum suction and illumination.

The single-piece intraoral device 200 generally includes integrated tongue and cheek retractor 240, bite piece 250, and connection section 570, each of which will be described in turn below. In alternative embodiments, one or more of the tongue and cheek retractor 240, bite piece 250, and connection section 570 are separate, connectable components.

The tongue and cheek retractor 240 has inner surfaces 260 and outer surfaces 270. The retractor 240 includes an incurved main body portion 280 and a forwardly angled cheek retractor (or "fish/whale tail") portion 290 joined by isthmus portion 300.

The retractor 240 includes an upper front flap 310, an upper rear flap 320, a lower front flap 330, and a lower rear flap 340. The front flaps 310, 330 and rear flaps 320, 340 are separated by an upper pocket opening or upper gap 350 and lower pocket opening or lower gap 360, respectively. The front flaps 310, 320 and the rear flaps 320, 340 (minus V-shaped grooves 416) respectively define envelopes that are the same and aligned with each other. The flaps 310, 320, 330, 340 all extend from and share a common, central spine 365. The spine 365 extends horizontally and longitudinally a majority of the length of the retractor 240 and divides the upper half 210 from the lower half 220 of the intraoral device 200. In addition to serving as the intersection location for the flaps 310, 320, 330, 340, in an embodiment of the intraoral device 200 where the intraoral device 200 is an intraoral illumination and vacuum suction device, the spine 365 may serve as a light pipe and act as a separator for an upper internal evacuation channel 418 above the spine 365 and a lower internal evacuation channel 419 below the spine 365.

In the embodiment shown, the front flaps 310, 330 have a flat, outer front surface with evacuation holes 410 therein and the rear flaps 320, 340 include curved, outwardly extending, vertical ridges 412 with no evacuation holes 410. On an interior surface of the ridges 412, respective incurved vertical channels 414 (with no evacuation holes 410, similar to ridges 412) are formed. In an alternative embodiment, an interior surface of the rear flaps 320, 340 include the incurved vertical channels 414 and an exterior surface of the rear flaps 320, 340 is substantially flat/smooth (i.e., does not include ridges 412). The evacuation holes 410 of the front flaps 310, 330 are vertically aligned with the ridges 412/channels 414, but the ridges 412/channels 414 do not include the evacuation holes 410. The ridges 412/channels 414 are not in the front flaps 310, 330. The channels 414 terminate at one end in spine 365 and at an opposite end terminate in V-shaped grooves or slots 416 in the rear flaps 320, 340 (at an intersection of the edges 380, 400 and the internal vertical channels 414 of the rear flaps 320, 340). There are no V-shaped grooves 416 in front flaps 310, 330. In an alternative embodiment, the grooves or slots 416 are U-shaped grooves. In further embodiments, the grooves 416 are only in front flaps 310, 330 or are in both the front flaps 310, 330 and the rear flaps 320, 340.

The ridges 412, which run along outer surface 270 of rear flaps 320, 340, terminate at opposite ends in the V-shaped grooves 416. In an alternative embodiment, there are no ridges 412, and V-shaped grooves 416 are smaller and simply cut into the flaps. The length of the channels 414 is about ½ the length of the ridges 412. In a preferred embodiment, the channels 414 and ridges 412 are vertical, not angled, and are perpendicularly disposed relative to spine 365. In alternative embodiments, the channels 414/ridges 412 are angled relative to spine 365.

In use, when vacuum forces imparted to the intraoral device 200 by a vacuum source cause the front flaps 310, 330 and the rear flaps 320, 340 to be drawn together, the channels 414 of the rear flaps 320, 340 remain in communication with the interior of the patient's mouth through the V-shaped grooves 416 and the evacuation holes 410 along the front flaps 310, 330 remain in communication with both the channels 414 and the interior of the patient's mouth. Thus, the evacuation holes 410 in the front flaps 310, 330 and rearwardly extending ridges 412/channels 414/V-shaped grooves 416 in the rear flaps 320, 340, in combination, do not close with oral-tissue blocking areas in the patient's mouth. Not having evacuation holes in the rear flaps 320, 340, and especially not having evacuation holes in the rear flaps 320, 340 aligned with the evacuation holes 410 of the front flaps 320, 340 prevents spray from a water three-way syringe from passing through the intraoral device 200 and into the patient's throat.

Figure 14:
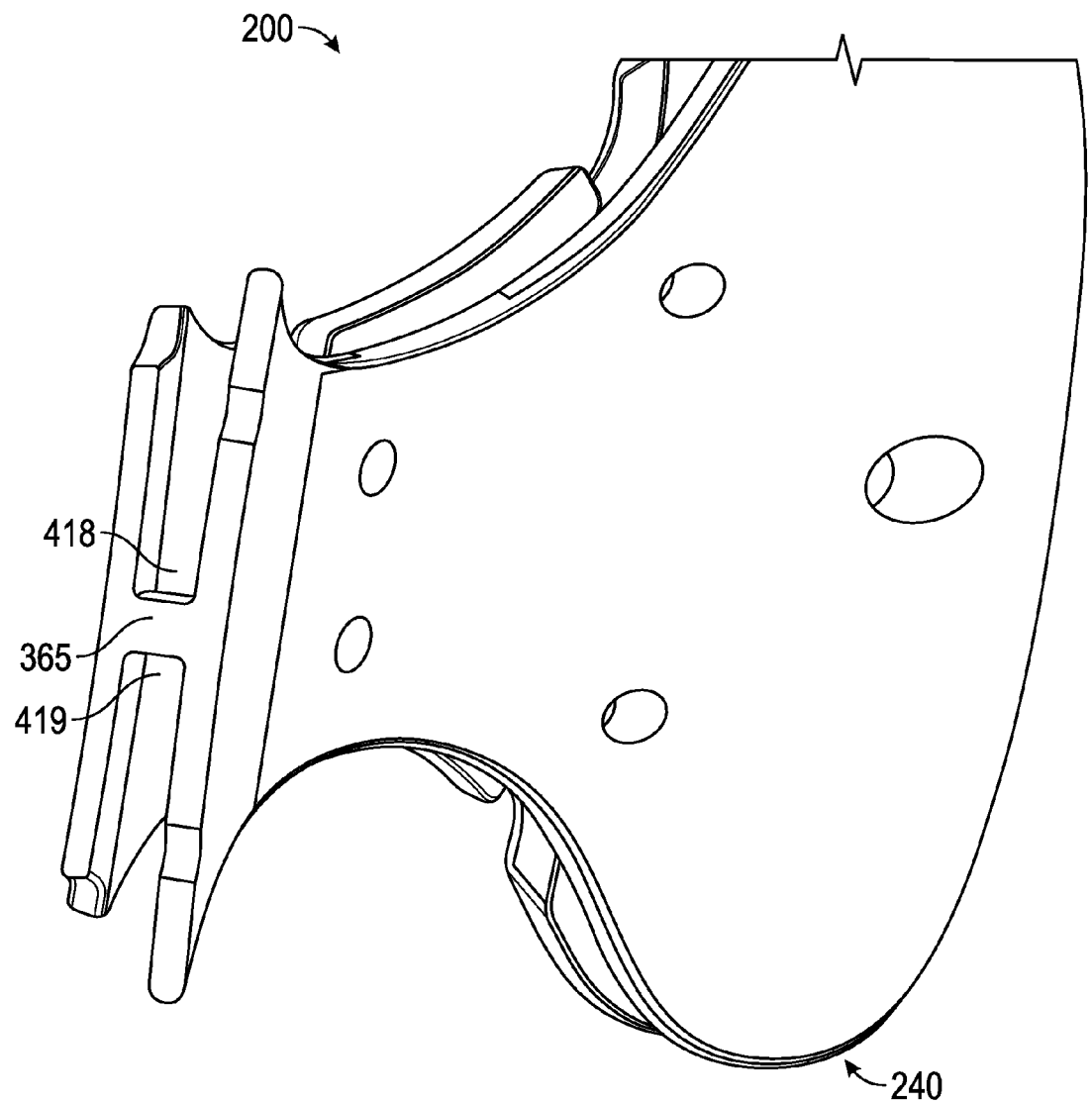
FIG. 14 is another cross-sectional view of the intraoral device.

FIG. 14 illustrate upper internal evacuation channel 418 and lower internal evacuation channel 419 adjacent the spine 365 that do not close (due to rigidity of spine 365) when the vacuum forces imparted to the intraoral device 200 by a vacuum source cause the front flaps 310, 330 and the rear flaps 320, 340 to be drawn together. FIG. 14 also illustrates the fluid path through the intraoral device 200 when the front flaps 310, 330 and the rear flaps 320, 340 are drawn together by the vacuum forces. The evacuation holes 410 in the front flaps 310, 330 and rearwardly extending ridges 412/channels 414/V-shaped grooves 416 in the rear flaps 320, 340, in combination, allow the upper internal evacuation channel 418 and lower internal evacuation channel 419 to be smaller than was possible in the past because of the improved communication between the channels 418/419 and interior of the patient's mouth caused by the evacuation holes 410, ridges 412/channels 414, and V-shaped grooves 416.

Although eight evacuation holes 410, four ridges 412, and eight channels 414 are shown, in alternative embodiments, the number and/or location of evacuation holes 410, ridges 412, and/or channels 414 may vary.

The upper front flap 310 and the upper rear flap 320 are configured to rest or flex against the paletal area or roof of the patient's mouth 36 during use. The upper roof of the mouth spans the upper gap 350 and pushes or bends the upper front flap 310 and the upper rear flap 320 forward to create a substantial seal along upper edges 370, 380, which are aligned with each other (excepted for the V-shaped grooves 416), creating a substantially sealed upper internal evacuation channel 418 in the upper gap 350, but yet still in communication with the patient's mouth through the evacuation holes 410 in the front flaps 310, 330 and the rearwardly extending ridges 412/channels 414/V-shaped grooves 416 in the rear flaps 320, 340. Similarly, the lower front flap 330 and the lower rear flap 340 are configured to rest or flex against the lingual area of mouth or tongue to keep the tongue protected and retracted during use. The tongue and floor of the patient's mouth span the lower gap 360 and forms a substantially seal along lower edges 390, 400, which are aligned with each other (excepted for the V-shaped grooves 416), creating a substantially sealed lower internal evacuation channel in the lower gap 360, but yet still in communication with the patient's mouth through the evacuation holes 410 in the front flaps 310, 330 and the rearwardly extending ridges 412/channels 414/V-shaped grooves 416 in the rear flaps 320, 340. Thus, in a non-vacuum state, the upper pocket opening 350 and lower pocket opening 360 are open and in a vacuum state the upper pocket opening 350 and lower pocket opening 360 are substantially sealed closed so that aspiration of fluids from the patient's mouth occurs through the evacuation holes 410 in the front flaps 310, 330 and the V-shaped grooves 416, which become fluid inlets for drawing fluids through the vertical channels 414, of the rear flaps 320, 340.

The cheek retractor portion 290 has an angled, curved, generally fish/whale-tail shape. In use, the cheek retractor portion 290 is flexed inward towards the main body portion 280 and rests against the inner cheek tissue between the cheek tissue and the outside of the teeth. With the cheek retractor portion 290 flexed, the upper flaps 310, 320 and lower flaps 330, 340 are closed together, forming a substantial seal along the upper edges 370, 380 and the lower edges 390, 400 of the retractor 240 adjacent where the isthmus portion 300 and cheek retractor portion 290 join, but yet still in communication with the patient's mouth through the evacuation holes 410 in the front flaps 310, 330 and the rearwardly extending ridges 412/channels 414/V-shaped grooves 416 in the rear flaps 320, 340.

When the tongue and cheek retractor 240 is positioned within the patient's mouth (similar to that shown in FIG. 1), the flexed upper flaps 310, 320, the flexed lower flaps 330, 340, and the flexed cheek retractor portion 290 form an envelope for isolating an area of interest in the patient's mouth and protect the upper roof, tongue and cheek of the patient's mouth from instruments such as dental drills during the dental procedure and prevent aspiration of debris or dropped items into the patient's throat.

The bite piece 250 includes symmetric, opposite tooth-engaging portions joined by an intermediate connection portion and allows for flexible, resilient, elastic movement of the tooth engaging portions in vertical, longitudinal, and lateral directions with respect to each other to allow vertical, longitudinal, and lateral biting movement by the patient for maximum biting comfort. The bite piece 250 includes a suction cavity 500 and a pair of vacuum holes 510 to allow a vacuum force to be provided in the cavity 500 for suctioning fluids in the area of the retro molar pad and the maxillary tuberosity of the patient's mouth.

The connection section 570 extends from the bite piece 250 and a proximal portion 580 of the retractor 240. The connection section 570 is configured to extend outside of a patient's mouth and attach to a multi-lumen vacuum connector/device for delivering vacuum suction (or vacuum suction and illumination) to the intraoral device 200.

The connection section 570 includes an open-ended tube 590 having a generally elliptical cross-section that tapers slightly in height as the tube 590 intersects the bite piece 250 and the proximal portion 580 of the retractor 240. An interior of the open-ended tube 590 defines a main vacuum channel 595. Adjacent the bite piece 250 and the proximal portion 580 of the retractor 240, the connection section 570 includes a cylindrical tube-shaped illumination connector 600 for transmitting light to the spine 365 and for supporting a plug portion of a vacuum connector. On opposite vertical sides of the illumination connector 600, where the illumination connector 600 joins the proximal portion 580 of the retractor 240, upper and lower vacuum ports 610, 620 communicate the main vacuum channel 595 with the upper and lower internal evacuation channels 418, 419 of the retractor 240. The main vacuum channel 595 communicates with the suction cavity 500 through the vacuum holes 510.

In use, the intraoral device 200 is inserted into the patient's mouth 202 so that the upper edges 370, 380 of the upper flaps 310, 320 contact an upper part of the patient's mouth 202 and the lower edges 390, 400 of the lower flaps 330, 340 contact a lower part of tongue within the mouth 202 of the patient; a vacuum state is applied to the intraoral device 200 so that the upper pocket opening 350 and lower pocket opening 360 are substantially sealed closed and the V-shaped grooves 416 become fluid inlets for drawing fluids through the vertical channels 414; and fluids from the patient's mouth are aspirated through the evacuation holes 410 in the front flaps 310, 330 and into the vertical channels 414 through the V-shaped grooves 416.

Although this invention has been described in terms of certain preferred embodiments, other embodiments apparent to those of ordinary skill in the art are also within the scope of this invention. Accordingly, the scope of the invention is intended to be defined only by the claims that follow.

What is claimed is:

1. An intraoral device, comprising:
a flexible body, comprising:
an upper front flap including an upper edge;
an upper rear flap forming an upper pocket with the upper front flap, the upper rear flap including an upper edge separated from the upper edge of the upper front flap to form an upper pocket opening;
at least one of the upper front flap and the upper rear flap including internal channels;
a lower front flap including a lower edge;
a lower rear flap forming a lower pocket with the lower front flap, the lower rear flap including a lower edge separated from the lower edge of the lower front flap to form an lower pocket opening;
at least one of the lower front flap and the lower rear flap including internal channels;
wherein the internal channels of at least one of the upper front and rear flaps and the lower front and rear flaps terminating in grooves along at least one of the upper edges and the lower edges, in a non-vacuum state the upper pocket opening and lower pocket opening are open, and in a vacuum state the upper pocket opening and lower pocket opening are substantially sealed closed so that aspiration of fluids from a patient's mouth occurs through the grooves, which become fluid inlets for drawing fluids through the internal channels.

2. The intraoral device of claim 1, further including evacuation holes in at least one of the front flaps and the rear flaps.

3. The intraoral device of claim 2, wherein the evacuation holes are in the front flaps and not in the rear flaps.

4. The intraoral device of claim 2, wherein the evacuation holes communicate with and are aligned with the internal channels.

5. The intraoral device of claim 1, wherein the grooves are in the rear flaps at an intersection of the edges and the internal channels of the rear flaps and not in the front flaps.

6. The intraoral device of claim 1, wherein the internal channels are vertical channels.

7. The intraoral device of claim 1, wherein the internal channels form corresponding external ridges in the rear flaps.

8. The intraoral device of claim 1, wherein the intraoral device includes a horizontally and longitudinally extending spine, an upper internal evacuation channel disposed above the spine in the upper pocket, and a lower internal evacuation channel disposed below the spine in the lower pocket.

9. The intraoral device of claim 8, wherein the intraoral device includes an upper portion above the spine and a lower portion below the spine that are vertically symmetrical.

10. The intraoral device of claim 1, wherein the lower rear flap and the upper rear flap define a profile, the lower front flap and the upper front flap define a profile, and the profile of the lower rear flap and the upper rear flap is the same as the profile of the lower front flap and the upper front flap except for the grooves.

11. A method of using the intraoral device of claim 1, comprising: inserting the intraoral device into a patient's mouth so that a upper edges of a upper flaps contact an upper part of the patient's mouth and the lower edges of the lower flaps contact a lower part of a tongue within the mouth of the patient; applying vacuum state to the intraoral device so that the upper pocket opening and lower pocket opening are substantially sealed closed and the grooves become fluid inlets for drawing fluids through the channels; aspirating fluids from the patient's mouth through the grooves in the intraoral device.

* * * * *